United States Patent
Sekine et al.

(10) Patent No.: US 6,177,065 B1
(45) Date of Patent: Jan. 23, 2001

(54) METHOD FOR PRODUCING AQUEOUS NAIL ENAMEL COMPOSITION

(75) Inventors: Masahiro Sekine, Yachiyo; Mitsuo Tamazawa, Matsudo; Takashi Sunamori, Funabashi, all of (JP)

(73) Assignee: Taisei Chemical Industries, Ltd., Tokyo (JP)

( * ) Notice: Under 35 U.S.C. 154(b), the term of this patent shall be extended for 0 days.

(21) Appl. No.: 09/352,399

(22) Filed: Jul. 14, 1999

(30) Foreign Application Priority Data

Oct. 15, 1998 (JP) ................................. 10-293946

(51) Int. Cl.$^7$ ...................................... A61K 7/04

(52) U.S. Cl. ................. 424/61; 424/61; 424/401

(58) Field of Search ........................ 424/61, 401

(56) References Cited

U.S. PATENT DOCUMENTS

| | | |
|---|---|---|
| 4,158,053 | 6/1979 | Greene et al. . |
| 4,301,046 * | 11/1981 | Schlossman ............................ 260/16 |
| 5,093,108 * | 3/1992 | Pappas et al. ........................ 424/61 |
| 5,102,654 * | 4/1992 | Castrogiovanni et al. ............ 424/61 |
| 5,110,584 * | 5/1992 | Medri et al. ........................... 424/61 |
| 5,294,435 | 3/1994 | Remz et al. . |
| 5,380,520 | 1/1995 | Dobbs . |
| 5,470,562 * | 11/1995 | Khamis .................................. 424/61 |
| 5,817,304 | 10/1998 | Mondet et al. . |
| 6,051,242 * | 4/2000 | Patel et al. ........................... 424/401 |

FOREIGN PATENT DOCUMENTS

| | | |
|---|---|---|
| 0593959 | 4/1994 | (EP) . |
| 2718350 | 10/1995 | (FR) . |

* cited by examiner

*Primary Examiner*—Thurman K. Page
*Assistant Examiner*—Liliana Di Nola-Baron
(74) *Attorney, Agent, or Firm*—Stevens, Davis, Miller & Mosher, L.L.P.

(57) ABSTRACT

Disclosed is a method for producing an aqueous nail enamel composition comprising the following procedure: an aqueous mixture which comprises, as essential components, water and a pigment of 3 μm or less in average particle size at a concentration of the pigment of 60% or less and is previously subjected to contact treatment with a substance having an ion exchangeability is kneaded under heating with a polyester polymer having a chemical structure containing a phenyl group and having a weight-average molecular weight of 2000–20000 and a softening point of 120° C. or lower in the state of the polymer being molten and simultaneously the volatile matter contained is removed under reduced pressure; the resulting mixture (A) comprising the polyester polymer and the pigment dispersed in the polyester polymer, said pigment finally having the inherent average particle size, is dissolved in an organic solvent at a concentration of the mixture (A) of 50% by weight or less; then the solution is mixed with an organic solvent solution (B) containing 80% or less of a resin containing 1–5 meq/g of a functional group capable of being dissociated to a cation or an anion; then the resulting mixture is neutralized and allowed to contact with a substance having ion exchangeability before and/or after carrying out phase inversion by dilution with addition of water to remove ionic impurities; the organic solvent is distilled off; and the residue is again allowed to contact with a substance having ion exchangeability to obtain an aqueous nail enamel composition comprising a color polymer composition dissolved in water alone as an essential component and containing less ionic impurities and substantially no organic solvent and film-forming aid. Thus, there is provided an aqueous nail enamel compositions which contains no organic solvent, is excellent in safety for human body and long-term storage stability, and has beautiful color and gloss, and high-coating film strength and adhesion.

3 Claims, No Drawings

METHOD FOR PRODUCING AQUEOUS NAIL ENAMEL COMPOSITION

BACKGROUND OF THE INVENTION

The present invention belongs to the field of aqueous nail enamel composition which contains no organic solvent, is excellent in safety for human body and long-term storage stability, and has beautiful color and gloss, and high strength and adhesion of coating film.

Conventional nail enamel compositions have the composition similar to that of organic solvent type paints. For example, they are usually composed of a resin such as a nitrocellulose and an alkyd resin, a pigment, a plasticizer and an organic solvent.

That is, the conventional nail enamel compositions are such that a pigment as a colorant is enclosed in a resin and suspended in an organic solvent, and the suspension is coated by some means and the organic solvent is volatilized to form a film. In this case, hardness of the film formed is adjusted by the remaining plasticizer. The film after use is removed by an organic solvent capable of dissolving the film.

However, since the nail enamel of the above composition contain organic solvents and plasticizers, they are used taking into consideration the restriction in use due to noxiousness to human body of the chemical substances used, the flammability of compounds in view of environmental safety, and the odor of organic solvents.

Under the circumstances, development of aqueous nail enamel compositions containing no organic solvent is demanded, and intensive effort for the development is exerted.

The present technical standard of means for making aqueous nail enamel compositions can be summarized as follows:

(1) To use water-soluble or water-dispersible resins as the constituting resins.

(2) To use organic solvents which are miscible with water as the solvents.

(3) To use hydrophilic compounds as the plasticizers.

(4) To use compounds like the above (3) as film-forming aids employed in using emulsion resins.

These efforts of development of aqueous nail enamel compositions are disclosed in Japanese Patent Nos.2686880 and 2115767 and JP-A Hei 8(1996)-225434.

However, even if the above means are employed, the conversion of the organic solvent type nail enamel compositions to aqueous nail enamel compositions still has the following technical problems to be solved.

(1) In the case of using a water-soluble resin as the resin to enclose pigment, it is difficult to design the resin to have a high refractive index because of the conditions for rendering the resin water soluble, and consequently high gloss and clear color are difficult to obtain.

(2) It is difficult to enclose separately and completely a plurality of pigments with a water-soluble resin with no bare pigment to be present.

(3) A smooth surface cannot be obtained without using a water-soluble organic solvent or a film-forming aid, and it is difficult to obtain a nail enamel composition comprising solely water.

(4) It is difficult to obtain a long-term storage stability for aqueous pigment dispersion.

(5) It is difficult to give a goodly endurable adhesive force to a nail having an oily surface using a hydrophilic resin.

SUMMARY OF THE INVENTION

The object of the present invention is to solve the above-mentioned five problems, the solution of which is essential for obtaining a practically usable aqueous nail enamel composition and thus to provide a stable aqueous nail enamel composition.

The technical idea of the present invention can be summarized as follows:

(1) Linear polymers are suitable for covering the surface of pigment, and since linear polymers are greater than branched polymers in entanglement between molecules at the same molecular weight, it can be expected that when the pigment is once enclosed with the linear polymer, the pigment is difficult to be bared.

(2) In the above case, it can be expected that a pigment dispersion having high gloss and clear color is obtained using a linear polymer having a phenyl group capable of increasing refractive index as the polymer for enclosing the pigment.

(3) Different polymers are used as the polymer which encloses the pigment and the polymer which has the function to water-solubilize or disperse in water the enclosed pigment, and the pigment is sufficiently dispersed in the polymer which is to enclose the pigment and this dispersion is used.

(4) If the polymer having the function to water-solubilize or disperse in water the enclosed pigment contains an organic solvent or a film-forming aid, since these compounds are merely mixed with the polymer and have the properties to govern the dissolving power of the polymer, pH of the system varies due to some external force, namely, evaporation, change in temperature, or absorption of an acidic substance such as carbon dioxide, and hence the dissolved state is disturbed to make the solution unstable with time. Therefore, unnecessary materials should not be allowed to be present.

(5) In order to secure adhesion to an oily surface, it is a matter of course that the polymer having the dispersing function should be hydrophobic, but, in this case, acid value or amine value decreases, resulting in reduction of dissolving power and increase of instability. In order to avoid the problems, it is considered that electrolytes should be excluded as much as possible for the removal of the salting-out action of impurity electrolytes which is a hindrance factor.

The inventors have made efforts to establish the above technical means and accomplished the present invention.

That is, the present invention is a method for producing an aqueous nail enamel composition comprising the following procedure: An aqueous mixture which comprises, as essential components, water and a pigment of 3 μm or less in average particle size at a concentration of the pigment of 60% or less and is previously subjected to contact treatment with a substance having an ion exchangeability is kneaded under heating with a polyester polymer having a chemical structure containing a phenyl group and having a weight-average molecular weight of 2000–20000 and a softening point of 120° C. or lower in the state of the polymer being molten and simultaneously the volatile matter contained is removed under reduced pressure; the resulting mixture (A) comprising the polyester polymer and the pigment dispersed in the polyester polymer, said dispersed pigment having finally the inherent average particle size, is dissolved in an organic solvent at a concentration of the mixture (A) of 50% by weight or less; then the solution is mixed with an organic solvent solution (B) containing 80% or less of a resin containing 1–5 meq/g of a functional group capable of being dissociated to a cation or an anion; then the resulting mixture is neutralized and allowed to contact with a substance having ion exchangeability to remove ionic impurities before and/or after carrying out phase inversion by dilution with addition of water; the organic solvent is distilled off; and the residue is again allowed to contact with a substance having ion exchangeability to obtain an aqueous nail enamel composition comprising a color polymer composition dissolved in water alone as an essential component and containing less ionic impurities and substantially no organic solvent and film-forming aid.

It can be additionally said that if impurity electrolytes are not contained, there is no need to take the trouble of carrying out the means to harden the dispersed particles for inhibition of coalescence and form a film with the aid of a film-forming agent.

DETAILED DESCRIPTION OF THE INVENTION

The technical idea of the present invention will be explained in more detail.

For the prevention of pigment from being suspended alone in a bare state in water, the first means of the present invention is to disperse the pigment in a phenyl group-containing polyester polymer which has nearly the linear form suitable for enclosing the pigment and has flexibility, is insoluble in water, and has a great refractive index, in such a state as faithful to the distribution of the particle size which the pigment inherently possesses.

The above means can be carried out by a high-speed dispersing machine such as a sand mill using a solution of the polymer as in usual means for preparation of paints, but this means requires a long-term dispersing step in order to obtain a dispersion which faithfully keeps the inherent distribution of the particle size which the pigment possesses, and thus this means is not preferred.

Therefore, according to the present invention, a hydrous paste (aqueous mixture) comprising a pigment and water is used, and the polymer and the hydrous paste of the pigment are directly kneaded with heating at a temperature at which the polymer is molten using a kneader provided with a pressure-reduction function, for example, by a means called flushing method, and the discharged water is removed by vacuum distillation, whereby the desired dispersion can be attained.

However, the difference from the usual flushing method is as follows: The hydrous paste of pigment is previously contacted with a substance having ion exchanging function selected depending on the characteristics of anion or cation of impurity electrolyte which agglomerates the pigment particles contained in the hydrous paste of the pigment, thereby to unravel the agglomeration, obtaining a particle size distribution close to the inherent particle size distribution possessed by the pigment. As a result, the time required for the dispersing step can be further shortened, and an effective dispersion can be performed.

By employing the above means, in the case of powdered dry pigment generally supplied which contains more agglomerated particles than the hydrous paste of the pigment, a dispersion having quality equal to the hydrous paste of the pigment can also be obtained by once making the powdered dry pigment to a hydrous paste and subjecting the paste to the same ion exchange treatment. This means is one of the constituent features of the present invention, and by this means it has become possible for the first time to provide an aqueous nail enamel composition which is safe for human body and beautiful in color.

For producing a water-soluble or water-dispersible nail enamel composition from the pigment dispersion obtained above, the dispersion is dissolved at a concentration as high as possible in an organic solvent capable of dissolving the polyester polymer constituting the dispersion to previously prepare a color solution. This solution is mixed with a resin solution which is an organic solvent solution or a hydrous organic solvent solution before neutralization and dilution with water and which becomes a water-soluble or water-dispersible resin solution after neutralization and dilution with water, so that there is given a ratio of the sum of the polymer content in the dispersion and the resin content in the resin solution to the pigment content which is suitable for forming a beautiful film on the nails as a nail enamel composition, and then the mixture is neutralized and diluted with water to obtain a water dispersion inverted in phase. The step of neutralization and dilution with water may be performed utilizing a mechanical force such as of high-speed homogenizer, but since the particles of the dispersion are in the state of liquid fine particles owing to the organic solvent incorporated from the color solution and they are unstable against a great mechanical shearing force, care should be taken not to cause coalescence of the particles.

The thus obtained dispersion is incomplete and it is necessary to remove impurities, namely, low molecular weight acids or bases which cause coalescence of the dispersed fine particles and which are incorporated from the water-soluble or water-dispersible resin by the method similar to that referred to in the preparation of the pigment dispersion. For this purpose, first, the dispersion is allowed to contact with a functional group which concerns with the water solubility or water dispersibility, for example, a substance having anion exchangeability in the case of anionic resin and a substance having cation exchangeability in the case of cationic resin, whereby a stable fine particle dispersion can be obtained. The ion exchanging process may be conducted after or before dilution with water if the dispersion has been neutralized. This process effectively proceeds even in an organic solvent if there is water contained in the ion exchange resin or the like.

After stability of the dispersion has been secured in this way, unnecessary organic solvent is distilled off with adding water and adjusting pH under reduced pressure to completely replace with water. Since the distillation brings about foaming, care should be taken of the construction of stirrer and distillation speed. Anti-foaming agents should not be used. In this step, a higher neutralization degree is preferred. Then, the resulting dispersion is allowed to contact with a substance having ion exchangeability to instantaneously and gently remove excess neutralizing agent without causing precipitation of the fine particles and to keep the dispersion at a low neutralization degree, and thus the present invention is completed. That is, if the neutralization degree is low, the dispersion becomes nearly hydrophobic, and this is effective for improvement of adhesion. The water-soluble and water-dispersible resins constituting the present invention may have any structure as far as they have affinity with the polyester polymer constituting the pigment dispersion, and the object can be attained by using styrene-acrylic acid resins which have a phenyl group and are water soluble or water dispersible.

The pigment dispersion used in the present invention is such that a pigment of particles having an average particle size of 3 µm or less is dispersed in a polyester polymer containing a phenyl group in chemical structure so that the dispersed particles have an average particle size of 3 µm or less which is inherently possessed by the pigment, although the particles may temporarily agglomerate to result in those of coarser particle size.

When the pigment used contains water and is in the form of paste, concentration of the pigment is adjusted to 60% or less, and when the pigment is in the dried state, it is made into a mixed solution with an organic solvent miscible with water and thereafter the solution is formed into a hydrous paste of 60% or less in pigment concentration using deionized water. The hydrous paste is allowed to contact with a substance having ion exchangeability to remove impurity electrolytes which cause the agglomeration of the pigment, and then kneaded with heating at a temperature higher than the softening point of the polymer in which the pigment is to be dispersed and under a reduced pressure of lower than 1 atm. Then, removal of water and dispersion of the pigment in the polymer are simultaneously carried out in a closed system, and the dispersion is cooled and taken out upon termination of complete removal of water, and finely ground.

Pigments usable in the present invention may be any of organic pigments and inorganic pigments which can be generally used for nail enamel compositions.

Examples of the organic pigments are azo pigments, phthalocyanine pigments and lakes such as Red No.202, Red No.220, Red No.226, Yellow No.4, Yellow No.5, Yellow No.401, and Blue No.404. Examples of the inorganic pigments are iron oxide, titanium oxide, and pearl pigments.

The polymers usable for attaining the object of the present invention are polyester polymers having a chemical structure containing phenyl group therein and having a softening point of 120° C. or lower and a molecular weight Mw=1000–50000, especially preferably 2000–20000.

These polyester polymers are selected because the melting point is definite and melting occurs sharply, and properties of the resulting film, such as gloss and clearness of color, are excellent and they enclose the pigment satisfactorily. Accordingly, vinyl chloride resin, acrylic resin, ethylene-vinyl acetate resin, cellulose acetate butyrate resin, modified polyethylene, etc. can be used each alone or in combination. Moreover, those which are modified with compounds such as urethane resin and epoxy resin can also be used if they satisfy the above conditions. In this case, sometimes plasticizers or solvents are needed as mentioned hereinafter.

In the present invention, the hydrous pigment paste is kneaded with the above resins under reduced pressure to disperse the pigment in the polymer which is in the fluidized state and simultaneously the discharged water is distilled off under reduced pressure. In this case, the polymer preferably has a softening point at which the polymer is sufficiently fluidized at a temperature of the step. However, because of the step being under reduced pressure, if softening is carried out with a solvent or plasticizer capable of being distilled off under reduced pressure, this can be distilled off together with water vapor, and thus even if the softening point of the polymer per se is high, the above step can be performed in the presence of the solvent or plasticizer which satisfies the above conditions. Preferred solvents or plasticizers are those which form azeotropic mixtures with water to be able to lower the temperature of the step to 120° C. or lower.

The solvents usable include, for example, methanol, ethanol, propanol, isopropyl alcohol, acetone, methyl ethyl ketone, methyl isobutyl ketone, cyclohexanone, methyl cellosolve, ethyl cellosolve, tetrahydrofuran, toluene, ethyl acetate, and butyl acetate. These can be used in such an amount as capable of plasticizing the polymer. However, the amount should be selected so that they can be removed by vacuum distillation.

As the substances having ion exchangeability usable in the present invention, there may be used any of commercially available ion exchange resins. In use, anion exchange resins can be activated to OH type and cation exchange resins can be activated to H type. The ion exchanging can be carried out by circulating a slurry of the hydrous paste diluted to a suitable concentration through a column packed with an ion exchange resin or by stirring the slurry together with an ion exchange resin in a tank, followed by filtration and separation. After ion exchange treatment, the slurry is subjected to centrifugal separation or concentration by a suitable filter medium.

Ion exchange fibers, ion exchange papers, and the like other than ion exchange resins can also be used as far as they have ion exchanging function.

Resins for converting the above pigment dispersion to an aqueous dispersion are those which contain 1–5 meq/g (per dry weight) of a functional group capable of being dissociated to ionic group of cation or anion by neutralization with an acid or a base. As the functional group capable of being dissociated to ionic group, mention may be made of, for example, acidic functional groups such as —COOH, —SO$_3$H, —OSO$_3$H, and —OPO(OH)$_2$, and basic functional groups such as primary amino group, secondary amino group and tertiary amino group. If the content of the functional group capable of being dissociated to ionic group is less than 1 meq/g, particle size of aqueous dispersion of polymer fine particles containing the pigment dispersion becomes coarser to cause settling or agglomeration with lapse of time, and this is not desired. If the content of the functional group capable of being dissociated to ionic group exceeds 5 meq/g, water resistance of the resulting aqueous manicure preparation obtained using a color resin composition of the polymer fine particles containing the pigment dispersion is inferior. In addition to the above ionic groups, nonionic hydrophilic groups such as —OH, —(CH$_2$CH$_2$O)$_n$—H, and —CONH$_2$ may also be contained as far as they do not adversely affect the properties of the aqueous dispersion such as water resistance. Examples of the resins include styrene-acrylic acid copolymer, hydrolyzates of styrene-maleic anhydride copolymer, reaction products of styrene-maleic anhydride copolymer and monohydric alcohol, copolymers of methacrylate or acrylate with acrylic acid or methacrylic acid, polyurethane containing a carboxylic acid, copolymer polyesters comprising sodium sulfo-isophthalate as a comonomer, and polyurethane containing a carboxylic acid—acrylic acid graft copolymer. These are not limiting. Furthermore, amphoteric resins having an acid group such as acrylic acid, methacrylic acid or itaconic acid and a basic functional group such as dimethylaminoethyl methacrylate together in the above composition can be used. Molecular weight is preferably Mw=3000–50000, especially preferably Mw=5000–100000 in terms of polystyrene. As for the glass transition temperature, the optimum value is selected depending on the properties finally required for the aqueous nail enamel compositions obtained from the color resin composition, and the glass transition temperature is not limiting.

The resin in the solution (B) is not necessarily composed of only one polymer component, but may be a mixture of two or more polymers. In the case of the mixture, the content of the functional group capable of being converted to ionic group in one polymer may exceed 5 meq/g, and the content of the functional group in the whole mixture can be in the range of 1–5 meq/g.

Next, explanation will be given on the procedure for making the pigment dispersion obtained by the above method to a water-soluble or water-dispersible dispersion.

First, the pigment dispersion is dissolved in an organic solvent at a concentration of 50% by weight or less. The organic solvent used is preferably a ketone solvent because the polymer in the dispersion is a polyester. Since this solvent is removed later by vacuum distillation, it is preferred to select one which has an azeotropic point with water of as low as possible.

Examples of the solvent are methyl ethyl ketone and methylisobutyl ketone. Moreover, mixed solvents of them with toluene may be used, but in this case, the mixing ratio must be determined so that the dispersion can be sufficiently dissolved therein.

Then, the resulting solution is mixed with the resin solution which is for conversion of the pigment dispersion to a water-soluble or water-dispersible dispersion, before neutralization and dilution with water. As to the mixing ratio in this case, the total of the content of the resin which is a binder for the pigment, namely, the content of the resin of the polymer coming from the pigment dispersion and the content of resin given from the resin solution should be determined taking into consideration the color density of the coating film, covering properties of the film and strength of the film.

The resin solution used here is a solution of the resin in preferably a single or mixed solvent such as of acetone or alcohol solvents, e.g., methanol, ethanol and isopropanol which are unlimitedly miscible with water so that the solution can be easily diluted with water, or hydrous solvents of these organic solvents containing some quantity of water.

Next, the color solution obtained by the mixing is neutralized. When an amphoteric electrolyte resin is used as the resin, the neutralization is unnecessary except for a special case.

As neutralizing agents, amines such as ammonia, monomethyldiethanolamine, dimethylethanolamine, and morpholine can be used in the case of anionic resins. Acetic acid is suitable as neutralizing agents in the case of cationic resins.

Preferred resins are anionic resins or amphoteric resins. Hereinafter, the steps of neutralization and dilution with water will be explained on anionic resins.

The step of dilution with water after neutralization is a step of phase inversion and hence is carried out under stirring with addition of water little by little at first and with raising the addition rate with progress of the phase inversion.

A high-speed homogenizer or an in-line homogenizer can be used effectively.

Since the fine particles constituting the dispersion are droplets containing organic solvent insoluble in water, the particles readily coalesce when subjected to a high shearing force, and care must be taken in this respect. The coalescence of the particles is also brought about by agglomeration of the particles caused by the action of salting-out of a slight amount of the electrolyte contained as explained hereinbefore with respect to the step of obtaining the pigment dispersion. Therefore, it is also effective here to carry out ion exchange for removal of the electrolyte. This step of ion exchange is effective when it is carried out before and/or after the dilution with water so far as it is carried out after neutralization. However, it is rather easy to produce fine particles when the ion exchange is carried out before dilution. This method may be carried out in accordance with the ion exchanging step explained before concerning the step of production of the pigment dispersion.

The thus obtained color dispersion is subjected to vacuum distillation with heating to completely remove the organic solvent contained. In this case, care should be taken on mechanics of stirring for defoaming, retention of pH of the system by replenishment for the evaporated neutralizing agent, and supplement of deionized water because this step is a concentration step.

Then, the amine as a neutralizing agent is removed to a limit from the resulting color dispersion by cation exchanging not so as to cause instantaneous sharp decrease of pH of the system and damage the dispersion stability. This step imparts hydrophobic property to secure properties such as adhesion to nail and fleshy hand.

According to the present invention, an aqueous nail enamel composition is provided which is equal to organic solvent type nail enamels in gloss, hardness of coating film and adhesion, is superior to conventional aqueous nail enamel compositions, and can be prevented from changing in structure which causes dissolution or discoloration of the pigment upon contact with water. Since no organic solvents are used, there are advantages of low flammability, no bad effect on the nail and no odor, and furthermore safety for human body can be enhanced by controlling the amount of the ionic impurities.

DESCRIPTION OF PREFERRED EMBODIMENTS

The present invention will be explained by the following examples.

SYNTHESIS EXAMPLE 1

120 Grams of methyl ethyl ketone, 180 g of isophorone diisocyanate, and 360 g of polycaprolactonediol were charged in a reaction vessel equipped with a reflux condenser, a dropping funnel, a thermometer, and a stirrer, and reaction was carried out for 3 hours in a nitrogen atmosphere with controlling the internal temperature to 90° C. Subsequently, 12 g of 2-hydroxyethyl methacrylate was added thereto, and the reaction was continued at 90° C. for 2 hours. Thereafter, 20 g of ethanol and 0.1 g of dibutyltin laurate were added, and the reaction was carried out for further 2 hours. After cooling, the reaction product was diluted with 270 g of methyl ethyl ketone. In this way, an urethane resin containing 60% of nonvolatile matter and having a double bond was obtained.

Then, 150 g of the resulting urethane resin containing a double bond and 100 g of methyl ethyl ketone were charged in the same reaction vessel as above and heated to the boiling point. In the dropping funnel were charged 60 g of styrene, 90 g of butyl acrylate, and 60 g of acrylic acid. Furthermore, in another dropping funnel were charged 12 g of azobisisobutyronitrile, 5 g of a chain transfer agent (NOHUMA-MSD manufactured by Nippon Oil & Fats Co., Ltd.), and 150 g of methyl ethyl ketone. With keeping the boiling point, the above monomer and the radical polymerization initiator were added dropwise separately from the dropping funnels over a period of 2 hours. The thus obtained acrylic acid-urethane graft copolymer had a solid content of 50.0%, a viscosity of 1.3 PS, and an acid value of 50.2 mg-KOH/g.

EXAMPLE 1

A mixture of 10.5% by weight of a red pigment (Red No.202), 18.5% by weight of ethanol, and 71.0% by weight of deionized water was well stirred for 30 minutes to prepare a pigment slurry.

To the pigment slurry were added 10% by weight of an ion exchange resin (trade name: SA-20A) activated to OH type and well washed with deionized water and hydro-extracted and 10% by weight of an ion exchange resin (trade name: WK-10) activated to H type and well washed with deionized water to remove fine powders of the ion exchange resin, followed by stirring gently for 30 minutes. Only the ion exchange resin was removed by a wire netting, and then the residue was filtered off by a broad cloth and the concentration was adjusted to 20% to obtain a pigment paste.

Then, 60% by weight of the resulting paste and 40% by weight of a polyester resin having a softening point of 110° C. and a weight-average molecular weight of about 9000 were introduced into a kneader. The mixture in the kneader was heated to 90° C. over a period of 20 minutes and then to 95° C. over a period of 10 minutes. With continuing the heating, pressure was gradually reduced, and water and the solvent were distilled off. The ultimate temperature was 120° C., the pressure was 250 mmHg, and the time required was 90 minutes. Then, the pressure was returned to atmospheric pressure, followed by cooling to obtain a blocky pigment dispersion.

80 Grams of the resulting pigment dispersion was dissolved in 50 g of methyl ethyl ketone in a beaker, and 360 g of the resin obtained in Synthesis Example 1 was added thereto, followed by stirring for 3 hours by a high speed impeller disperser. The average particle size measured by laser beam scattering method (by means of "Microtrac" manufactured by Nikkiso Co., Ltd.) was 0.1 µm.

The total amount of the dispersion was charged in a beaker, and thereto was gradually added dropwise 36.5 g of 28% aqueous ammonia with stirring at room temperature to perform neutralization. Then, thereto was added 10 g of an anion exchange resin (SA-20A; manufactured by Mitsubishi Chemical Co., Ltd.) activated to OH type, washed with deionized water, and subjected to sufficient hydro-extraction, followed by gentle stirring for 30 minutes. Only the ion exchange resin was removed by a wire netting and the total of the residue was introduced into a flask. With stirring at room temperature, 230 g of deionized water was gradually added dropwise to cause phase inversion.

With continuing the stirring, the organic solvent was recovered by distillation under reduced pressure. In this case, the procedure was carried out with occasionally monitoring the pH value and further supplying deionized water. As a result, an aqueous polymer color composition of 33.3% in solid content was obtained.

100 Grams of the resulting aqueous polymer color composition and 10 g of anion exchange resin SA-20A (manufactured by Mitsubishi Chemical Co., Ltd.) activated to OH type, washed with deionized water and subjected to sufficient hydro-extraction were both introduced into a beaker, followed by gentle stirring for 30 minutes. The ion exchange resin was removed by a gauze to obtain a hydrous polymer color composition from which ionic impurities were removed.

Formulation of an aqueous nail enamel composition using the above aqueous polymer color composition was as follows:

| | |
|---|---|
| Aqueous polymer color composition | 100 parts by weight |
| Silicone deforming agent (trade name BYK-023; manufactured by BYK Chemie Co.) | 0.05 part by weight |
| Deionized water | optional amount |

EXAMPLE 2

In a beaker were charged 100 g of the pigment dispersion of Example 1, 60 g of a styrene-acrylic acid copolymer (trade name "JONCRYL 68" manufactured by Jonson Co., Ltd.; acid value=150 mg-KOH/g, and weight-average molecular weight Mw=800), and 120 g of ethyl acetate, followed by stirring for 3 hours by a high speed impeller disperser. The average particle size was 0.1 µm measured by the same method as in Example 1. The total amount of the dispersion was charged in a flask, and thereto was gradually added dropwise 10 g of 28% aqueous ammonia with stirring at room temperature to perform neutralization. Successively, 250 g of deionized water was gradually added dropwise to cause phase inversion. With continuing the stirring, the organic solvent was recovered under reduced pressure to obtain an aqueous polymer color composition of 38.1% in solid content.

An aqueous nail enamel composition was prepared using 17.4% by weight of the above aqueous polymer color composition, 58.3% by weight of an aqueous polymer emulsion (trade name "SE-1690E" manufactured by Taisei Chemical Industries, Ltd.; solid content: 40%), and the other additives which were the same as in Example 1.

EXAMPLE 3

A blocky pigment dispersion was obtained by carrying out the kneading as in Example 1 using a yellow pigment (Yellow No.4) as a pigment.

In the same manner as in Example 1 except for using the resulting pigment dispersion, neutralization and phase inversion were carried out to obtain an aqueous polymer color composition of 28.7% in solid content. An aqueous nail enamel composition was prepared using 13.9% by weight of the resulting aqueous polymer color composition, 66.3% by weight of the aqueous polymer emulsion, and the other additives which were the same as in Example 1.

Comparative Example 1

45% by weight of a nitrocellulose resin (NC. RS 1/4 (FQ cotton)) and 45% by weight of a red pigment (Red No.202) were mixed for 5 minutes by an open kneader, and, then, 10% by weight of a plasticizer (dibutyl phthalate) was added thereto, followed by stirring for 15 minutes to obtain a blocky compound. This compound was fed to a twin-roll mill (manufactured by Inoue Seisakusho Co., Ltd.) and fluidized with addition of 13.6% by weight of butyl acetate, and then formed into a sheet. The resulting sheet was folded to again form a sheet, and this operation was repeated 50 times. The obtained sheet was cut to chips having edges of 3 mm by a pelletizer to obtain a pigment dispersion. In the same manner as in Example 1 except for using the resulting pigment dispersion, the neutralization and phase inversion were carried out to obtain an aqueous polymer color composition of 28.7% in solid content. An aqueous nail enamel composition was prepared using 13.5% by weight of the above aqueous polymer color composition, 65.3% by weight of the aqueous polymer emulsion, and the other additives which were the same as in Example 1.

Comparative Example 2

An aqueous nail enamel composition was prepared using 13.5% by weight of the aqueous polymer color composition obtained without carrying out all of the ion exchanges in Example 1, 65.3% by weight of the aqueous polymer emulsion, 6.0% by weight of diethylene glycol diethyl ether as a film forming aid, 2.5% by weight of acetyltributyl citrate as a plasticizer, and the other additives which were the same as in Example 1.

Comparative Example 3

70% by weight of an aqueous solution of styrene-acrylic acid resin (HIGHROS H-2190) adjusted to 30% in solid content was mixed with 9% by weight of a yellow pigment (Yellow No.4) and 21% by weight of deionized water, followed by stirring for 30 minutes by a high speed impeller disperser. Then, 160 ml of the mixture and glass beads (1 mmø) of the same volume were charged in a sand grinder (manufactured by Aimex Co., Ltd.) and dispersed for 1 hour at a rotation speed of 1600 rpm to obtain a pigment dispersion of 30.0% in solid content. An aqueous nail enamel composition was prepared using 11.1% by weight of the resulting dispersion, 66.7% by weight of the aqueous polymer emulsion, and the other additives which were the same as in Example 1.

The aqueous nail enamel compositions obtained in the examples and comparative examples were evaluated on gloss, drying characteristics, adhesion, water resistance and others by the following evaluation methods.

(1) Gloss

The aqueous nail enamel composition was coated on a nail and dried under the conditions of 25° C. in temperature and 60% in relative humidity, and after lapse of 4 hours, the coating film was visually examined. The results were evaluated by the following three grades.

○: Good
Δ: Average
X: Bad (2) Reproducibility of Color

The aqueous nail enamel composition was coated on a nail and dried under the conditions of 25° C. in temperature and 60% in relative humidity, and after lapse of 4 hours, the coating film was visually examined on the degree of reproduction of the inherent color of the pigment. The results were evaluated by the following three grades.

◎: Good
○: Average
X: Bad (3) Drying Characteristics

The aqueous nail enamel composition was coated on a nail and dried under the conditions of 25° C. in temperature and 60% in relative humidity, and the state of drying of the coating film was examined by touching the surface. The results were evaluated by the following three grades.

◎: A time of 2 minutes or more and less than 3 minutes was required for drying.

○: A time of 3 minutes or more and less than 4 minutes was required for drying.

X: A time of 4 minutes or more was required for drying.

(4) Hardness of Coating Film

The aqueous nail enamel composition was coated on a glass plate by an applicator and dried under the conditions of 25° C. and 60% in relative humidity, and after lapse of 4 hours, pencil hardness of the coating film was measured.

(5) Adhesion

The aqueous nail enamel composition was coated on a glass plate by an applicator and dried under the conditions of 25° C. and 60% in relative humidity, and after lapse of 4 hours, the coating film was cut to make 10×10 squares. Thereafter, an adhesive cellophane tape was applied to the coating film, and, then, the tape was removed. The state of peeling of the squares was examined. The results were evaluated by the following two grades.

○: No squares were peeled off.
X: Squares were peeled off.

(6) Water Resistance of Pigment

The aqueous nail enamel composition was coated on a nail and dried under the conditions of 25° C. in temperature and 60% in relative humidity, and after lapse of 4 hours, the coating film was removed by a usual remover, and degree of stain of the nail caused by the dissolved pigment was visually examined. The results were evaluated by the following two grades.

○: No stain occurred.
X: Stain occurred.

TABLE 1

|  | Example 1 | Example 2 | Example 3 | Comparative Example 1 | Comparative Example 2 | Comparative Example 3 |
| --- | --- | --- | --- | --- | --- | --- |
| Gloss | ○ | ○ | ○ | Δ | ○ | Δ |
| Color reproducibility | ◎ | ○ | ○ | x | x | x |
| Drying characteristic | ◎ | ○ | ○ | ○ | x | ○ |
| Film hardness | HB | HB | HB | HB | 2B | B |
| Adhesion | ○ | ○ | ○ | ○ | ○ | x |
| Water resistance of pigment | ○ | ○ | ○ | x | ○ | x |

As can be seen from Table 1, the aqueous nail enamel composition of the present invention are excellent in gloss, drying characteristics, hardness and adhesion of the coating film, and even the pigment of inferior water resistance can be improved in the water resistance when the pigment is formulated into the aqueous polymer color composition of the present invention. Furthermore, safety for human body can be improved by controlling the amount of the ionic impurities.

What is claimed is:

1. A method for producing an aqueous nail enamel composition which comprises kneading under heating an aqueous mixture comprising, as essential components, water and a pigment of 3 μm or less in average particle size at a concentration of the pigment of 60% or less and previously subjected to contact treatment with a substance having ion exchangeability, with a polyester polymer having a chemical structure containing a phenyl group and having a weight-average molecular weight of 2000–20000 and a softening point of 120° C. or lower in the state of the polymer being molten and simultaneously removing the volatile matter contained under reduced pressure; dissolving the resulting mixture (A) comprising the polyester polymer and the pigment dispersed in the polyester polymer, said pigment having finally the inherent average particle size, in an organic solvent at a concentration of the mixture (A) of 50% by weight or less; mixing the resulting solution with an organic solvent solution (B) containing 80% or less of a resin containing 1–5 meq/g of a functional group capable of being dissociated to a cation or an anion; neutralizing the resulting mixture and allowing the mixture to contact with a substance having ion exchangeability to remove ionic impurities before and/or after carrying out phase inversion by dilution with addition of water; distilling off the organic solvent; and again allowing the residue to contact with a substance having ion exchangeability to obtain an aqueous nail enamel composition comprising a color polymer composition dissolved in only water as an essential component and containing less ionic impurities and substantially no organic solvent and film-forming aid.

2. A method for producing an aqueous nail enamel composition according to claim 1, wherein the resin containing 1–5 meq/g of the functional group is an acrylic resin containing a styrene group.

3. An aqueous nail enamel composition obtained by the method of claim 1.

* * * * *